(12) United States Patent
Ducree et al.

(10) Patent No.: US 10,537,890 B2
(45) Date of Patent: Jan. 21, 2020

(54) MICROFLUIDIC DEVICE

(71) Applicant: DUBLIN CITY UNIVERSITY, Dublin (IE)

(72) Inventors: Jens Ducree, Ashbourne (IE); Macdara Glynn, Galway (IE); Charles Nwankire, Stillorgan (IE)

(73) Assignee: Dublin City University, Dublin (IE)

( * ) Notice: Subject to any disclaimer, the term of this patent is extended or adjusted under 35 U.S.C. 154(b) by 254 days.

(21) Appl. No.: 15/543,889

(22) PCT Filed: Jan. 12, 2016

(86) PCT No.: PCT/EP2016/050475
§ 371 (c)(1),
(2) Date: Jul. 14, 2017

(87) PCT Pub. No.: WO2016/113257
PCT Pub. Date: Jul. 21, 2016

(65) Prior Publication Data
US 2017/0368550 A1  Dec. 28, 2017

(30) Foreign Application Priority Data

Jan. 15, 2015 (GB) .................................. 1500672.9

(51) Int. Cl.
| | | |
|---|---|---|
| *G01N 15/02* | (2006.01) | |
| *B01L 99/00* | (2010.01) | |
| *B01L 3/00* | (2006.01) | |

(52) U.S. Cl.
CPC ..... *B01L 3/502761* (2013.01); *B01L 3/50273* (2013.01); *G01N 15/0272* (2013.01); *B01L 2200/0652* (2013.01); *B01L 2300/0803* (2013.01); *B01L 2300/0864* (2013.01); *B01L 2400/0409* (2013.01); *G01N 2015/0288* (2013.01)

(58) Field of Classification Search
None
See application file for complete search history.

(56) References Cited

U.S. PATENT DOCUMENTS

| | | |
|---|---|---|
| 2006/0035386 A1 | 2/2006 | Hattori et al. |
| 2007/0026419 A1 | 2/2007 | Fuchs et al. |
| 2007/0160503 A1* | 7/2007 | Sethu .................. A61M 1/3633 422/400 |
| 2009/0173700 A1 | 7/2009 | Auner et al. |
| 2012/0040843 A1 | 2/2012 | Ducree et al. |

(Continued)

FOREIGN PATENT DOCUMENTS

| | | |
|---|---|---|
| WO | 02/42780 A2 | 5/2002 |
| WO | 2004/113877 A1 | 12/2004 |
| WO | 2011/079217 A1 | 6/2011 |

OTHER PUBLICATIONS

Combined Search and Examination Report under Sections 17 and 18(3), dated Jul. 16, 2015, for British Application No. GB1500672.9, 5 pages.

(Continued)

*Primary Examiner* — Paul S Hyun
(74) *Attorney, Agent, or Firm* — Cozen O'Connor (57) ABSTRACT

Microfluidic devices that are configured to use centrifugal forces to bias particles into one or more capture regions based on their individual sizes are described.

20 Claims, 4 Drawing Sheets

(56) References Cited

U.S. PATENT DOCUMENTS

2013/0210599 A1  8/2013  Wo et al.
2014/0045249 A1  2/2014  Yao et al.
2014/0248621 A1  9/2014  Collins

OTHER PUBLICATIONS

International Search Report, dated Apr. 1, 2016, for PCT/EP2016/050475, 3 pages.
Written Opinion, dated Apr. 1, 2016, for PCT/EP2016/050475, 8 pages.

* cited by examiner

MICROFLUIDIC DEVICE

FIELD OF THE INVENTION

The present invention relates to microfluidic devices and in particular to microfluidic devices that are configured to selectively sort particles of different sizes. The present invention more particularly relates to microfluidic devices that are configured to use rotationally induced inertial forces such as the centrifugal force to bias particles into one or more capture regions based on their individual sizes.

BACKGROUND

Microfluidic devices are well known and are used for a variety of purposes including applications such as lab-on-a chip systems. A microfluidic chip includes at least one channel having at least one dimension of the order of micrometers or tens of micrometers. These channels are typically formed in a substrate such as glass, silicon or a polymer such as PDMS. Individual channels that form the microfluidic chip are in fluid communication with one another and may be connected to achieve a desired effect such as a mixing, pumping, redirection or allowing specific chemical reactions to occur within the chip.

It is known to fabricate such microfluidic chips on a rotatable substrate so as to use an induced centrifugal field resultant from a rotation of the substrate to bias fluid movement within the channels of the chip. Such a force acts outwardly from an axis of rotation of the substrate such that during rotation of the substrate a fluid within a microfluidic channel will tend to move out and away from the axis of rotation of the substrate towards a circumference of the substrate. It will be appreciated that the actual force is in a direction parallel to radial lines extending outwardly from the axis of rotation but the fluid motion will be constrained by the actual pattern of the channels within which it flows.

In an earlier patent application of the instant applicant—US2012040843A1—there is described a microfluidic device that uses an array of single-cell capture traps which resemble cups in the geometry of a letter "V". These capturing structures are placed in the sedimentation path of a cellular sample when processed using centrifugal forces to migrate a cell population microfluidic chip in a stopped-flow where the suspending liquid is essentially at rest with respect to the rotating substrate. Using such an arrangement it is possible to isolate and enumerate a number of candidate particles or groups of particles. Example of such particles are circulating tumour cells (CTCs). A CTC is a cell that has detached from a solid tumour and entered into the peripheral bloodstream. Recent progress in the field of oncological diagnostics, however, has also identified the presence of multi-cellular clusters of CTCs in the blood as a key diagnostic and prognostic of patient fate, particularly in terms of development of resistance to chemotherapy. These cells are present in a sample of blood and using a device per the teaching of US2012040843A1 it is possible to identify these cells at single-cell resolution, following sample preparation using a negative-isolation mode of CTC enrichment. However, due to the single-cell resolution, the V-cup strategy is not suitable for isolation of multi-cellular events but the fact remains that it is desirable to be able to accurately detect such CTCs.

Current commercial devices for the detection of CTCs are based on "positive-mode" isolation where cells are directly targeted based on assumed phenotypes. These arrangements require a physical or molecular bias, such that the techniques require knowledge of the phenotype of candidate cells within a sample in order to capture the cells of interest. It would be useful if CTCs or other target molecules could be isolated without such bias.

Other techniques aim to isolate candidate cells via assumed bio-physical properties of candidate CTCs and are typically based on the presumed increased size of such cells. Such systems mediate size filtration by a porous filter or a track-etched membrane. These membranes are designed and directed at enriching CTCs that exist as single cells, and cannot distinguish between a potential CTC cell cluster and a collection of single cells that strike and resolve to the membrane at the same point but exist as single cells in the blood.

Hence, there continues to be a need for devices and methodologies that would facilitate the targeted selection of molecules or groups of molecules based on their physical dimensions.

SUMMARY

To address these and other issues the present teaching provides a device and methodology that allows selection of a distribution of CTC events ranging from single cells, through medium clusters and up to large multi-cell events into quantifiable bins, while simultaneously ensuring minimal occurrence of cell packing within the chip that can introduce errors of inappropriate scoring of clusters. Evidently the technology could also be applied to other cell types displaying a propensity to clustering.

Accordingly the present teaching provides a device and method in accordance with the claims that follow.

DETAILED DESCRIPTION OF THE DRAWINGS

Using a device and method per the present teaching it is possible to isolate and characterise cluster sizes from liquid biopsy that will have the highest potential in clinical diagnostics, particularly in the areas of oncology. There is also potential for commercial application to research institutes who will require the isolation of clusters as material for further biomedical studies. The present teaching will be described in the following with specific reference to the isolation and identification of CTCs but it will be appreciated that other particles of interest could equally be sorted using a size selection arrangement per the present teaching. For example a system and methodology in accordance with the present teaching could be utilized in detection of occurrences of clusters in response to clotting events. These events are known to form within blood for example as a consequence of surgery. As a general characterisation, it will be appreciated that a system and method in accordance with the present teaching may be used to specifically target cellular events that comprise of more than one cell, where all component cells are physically associated with the event.

Figure 1:
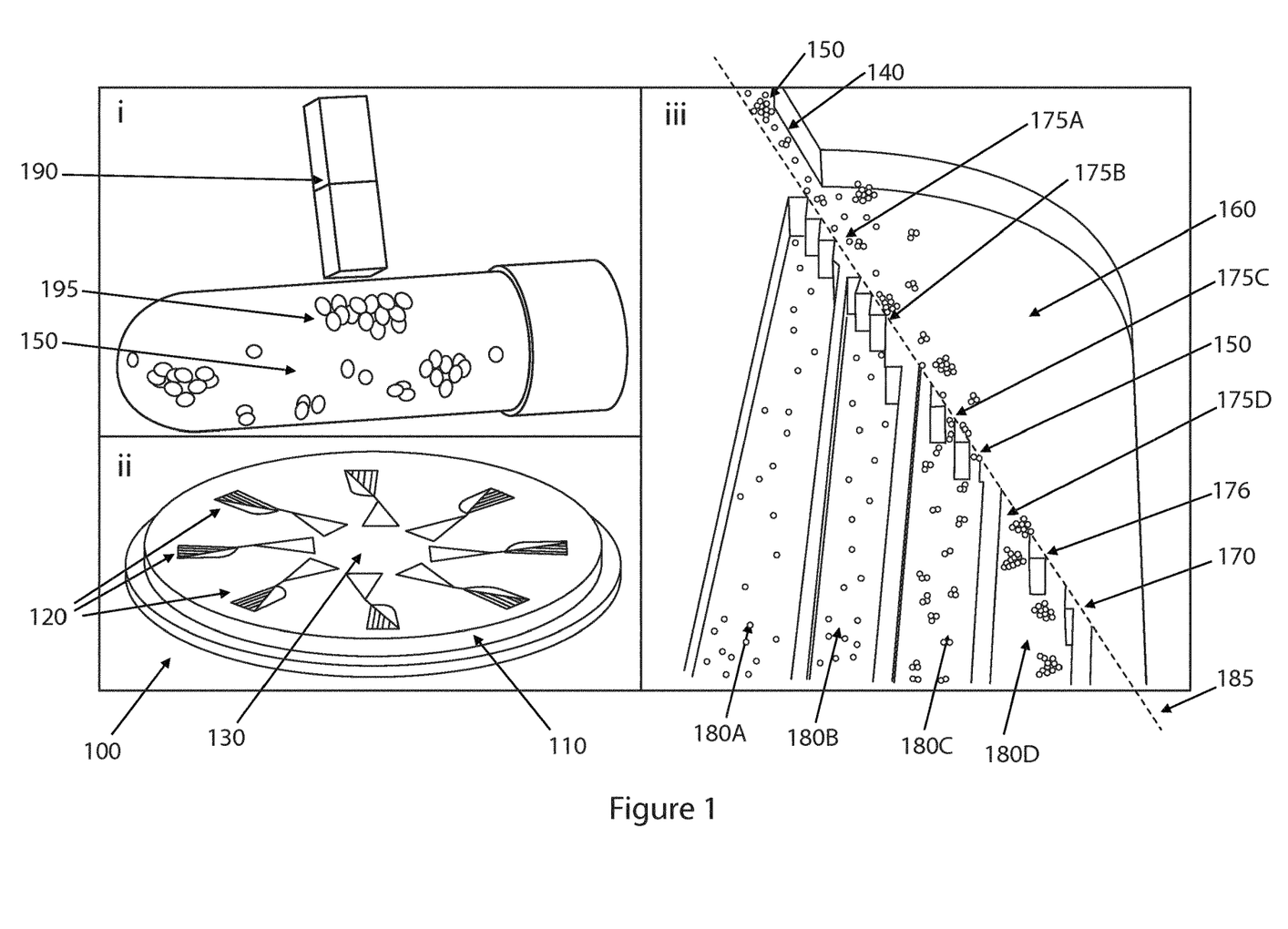
FIG. 1 shows an exemplary set of equipment that may be used for particle analysis in accordance with the present teaching with FIG. 1 (*i.*) showing an apparatus that may be used for removal of healthy white blood cells, WBCs (grey), by negative selection such that candidate clusters remain in solution, FIG. 1 *ii*) is a schematic representation of a microfluidic device with 8 chambers provided on a rotatable substrate in accordance with the present teaching and FIG. 1 (*iii*) is a schematic representation of microfluidic channel incorporating a bias rail to provide event isolation by size exclusion within one of the 8 chambers shown in FIG. 1 (*ii*)

FIG. 1 shows an example of a microfluidic device 100 comprising a rotatable substrate 110 comprising a set of individual microfluidic sorting chambers 120 provided in accordance with the present teaching. In the example of FIG. 1(ii), eight individual sorting chambers 120 are provided and it will be appreciated that this number is purely exemplary and any number of sorting chambers could be provided on the substrate 110 dependent on the desired application or use of the device 100. The individual sorting chambers 120 are circumferentially arranged about an axis of rotation 130 of the substrate 120.

As shown in FIG. 1(iii) which shows an example of one of the plurality of chambers of FIG. 1(ii), a chamber 120 comprises an inlet 140 within which a fluid comprising particles of interest 150 may be introduced. The chamber is desirably orientated on or in the substrate such that the inlet 140 is provided proximal to the axis of rotation of the substrate. In this way rotation of the substrate will provide a centrifugal force that will bias particles within the fluid that is introduced into the inlet into and through a chamber sorting area 160.

The chamber 120 comprises a size exclusion or bias rail 170 that gates the entry of cellular events into a series of collection bins 180 positioned radially outward of the rail. In this example of FIG. 1, four individual collection bins 180A, 180B, 180C, 180D are illustrated but again it will be appreciated that this number of collection bins is illustrative as opposed to intended to be limiting.

The bias rail is a segmented rail comprising a plurality of apertures 175A, 175B, 175C, 175D that are spaced along the axis 185 of the bias rail. The rail extends from the inlet 140 of the chamber and is orientated such that operably the induced centrifugal force will bias particles entering the chamber towards and along the rail as they migrate through the chamber sorting area 160. Each of the apertures provide an inlet for a corresponding collection bin 180A, 180B, 180C, 180D and the dimensions of the apertures determine the size of particles of interest 150 that may pass through the gate that is defined by a specific aperture and into the collection bin. In accordance with the present teaching, the dimensions of the apertures increase with the increased radial distance away from the axis of rotation. In this way smaller particles of interest will be collected initially in a first collection bin 180A, then a next set of particles of interest into a second collection bin 180B until the largest particles are collected in the last bin 180D which is furthest from the inlet 140.

In this way, rather than resolving captured events to a defined positional locus on the substrate, the size exclusion rail sorts and distributes all isolated target events into predetermined capture bins. Each of the capture bins 180 harbour multi-cellular events within a size range defined by aperture gaps of specific widths in the rail 170 that gate entry of a cellular event to the underlying bin. The widths of the apertures are selected to provide a resolution capable of delivering a resolution where cellular clusters with a size range from for example 1 to 8+ cells can be sorted, thus allowing an operator to generate a metric that provides knowledge pertaining to the range of clusters harboured in a sample, and also the distribution of the cluster sizes present.

It will be appreciated that in order to selectively sort particles of interest within a fluid sample certain pre-processing steps may be required. The number and type of steps will vary on the material that is being targeted. In the example of identification of CTCs that may be present in a whole blood sample, e.g. as obtained from a patient, the process can be divided into two phases. One phase is an off-chip sample processing step where material and volume reduction occurs, and the second phase involves size-sorting the target events isolated from the first phase using the size exclusion rail on a microfluidic centrifugal substrate.

Phase 1: Sample Processing

A typical whole blood volume required for cell-cluster diagnostics can range from 1 ml to 10 ml. However, this volume is in excess of what is feasible to process on a discrete (i.e. fully contained with no external pumps) microfluidic device. Phase 1 therefore reduces both the volume of the sample, and also the vast amount of background material inherent to a blood sample. Standard protocols are used for these tasks, with hypotonic red blood cell lysis being used for the former, and magnetic-bead based negative mode isolation being used for the latter.

Phase 1 Description and Workflow

Whole blood is extracted to anti-coagulation tubes as per standard protocol.

Red blood cells, RBCs, are removed using hypotonic lysis per standard protocols, and white blood cells, WBCs, are isolated by centrifugation.

Negative Isolation Protocol:

WBCs are incubated with super-paramagnetic beads with specificity for CD15 (granulocytes) and CD45 (all WBC types).

Figure 2:
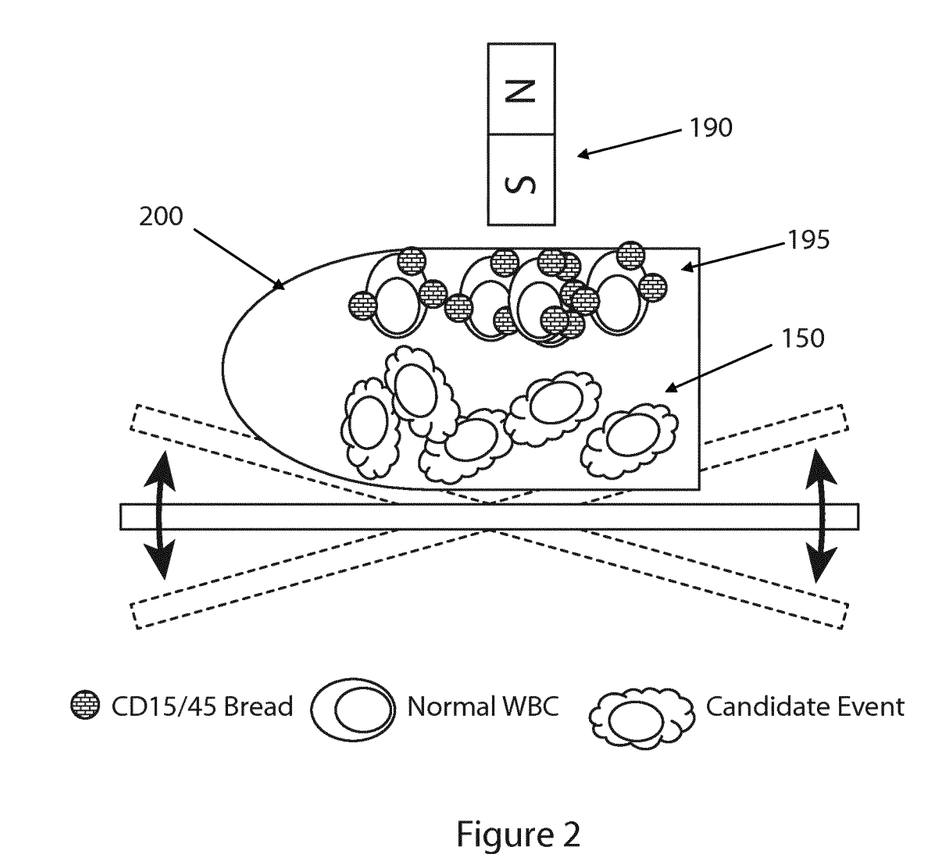
FIG. 2 is a schematic providing additional detail on the arrangement previously illustrated in FIG. 1(*i*) which provides for negative isolation of the particles of interest.

While rocking the incubation tube horizontally, a strong permanent magnet 190 is slowly brought into proximity of the edge the tube to immobilise the beads/WBCs 195 to the inner surface of the tube. The remaining solution (containing any candidate events 150) is then removed to a fresh sample storage tube (FIG. 2).

Candidates in the sample storage tube 200 are then concentrated by centrifugation and re-suspension in a small volume of sample buffer. This may be achieved using conventional methodologies and for the ease of explanation is not represented in FIG. 2

Optional: Cells may be stained specifically (using antibodies directed against specific epitopes) or non-specifically (i.e. using nuclear staining for identification of nucleated cells).

Phase 2 Description and Workflow

Phase 2 uses a centrifugal-microfluidic device to size-sort the multicellular clusters isolated from phase 1 into discrete collections of events of a defined size range. The device here described is purposely designed for specifically targeting and sorting multicellular clusters as its primary role.

As described above a microfluidic size sorting device 100 provided in accordance with the present teaching comprises a rotatable substrate 110 containing a number of discrete sampling chambers 120. Each chamber contains a sample loading area 301 that is coupled to the inlet 140 in the form of a focusing channel that extends to a chamber sorting area 160, a rail 170 that runs continuously from the focusing channel to an overflow structure, and individual discrete sample collection chambers (FIG. 1ii) that are capped by the rail. Each chamber is first fluidically primed before the processed sample from phase 1 is distributed equally between all chambers by loading aliquots to the Sample Loading area. Once loaded, the disc is rotated at 12 Hz. It will be appreciated that this frequency is exemplary of the type of rotational speeds that may be utilized in the context of the present teaching and other applications of the present teaching may utilize different rotational frequencies.

Figure 3:
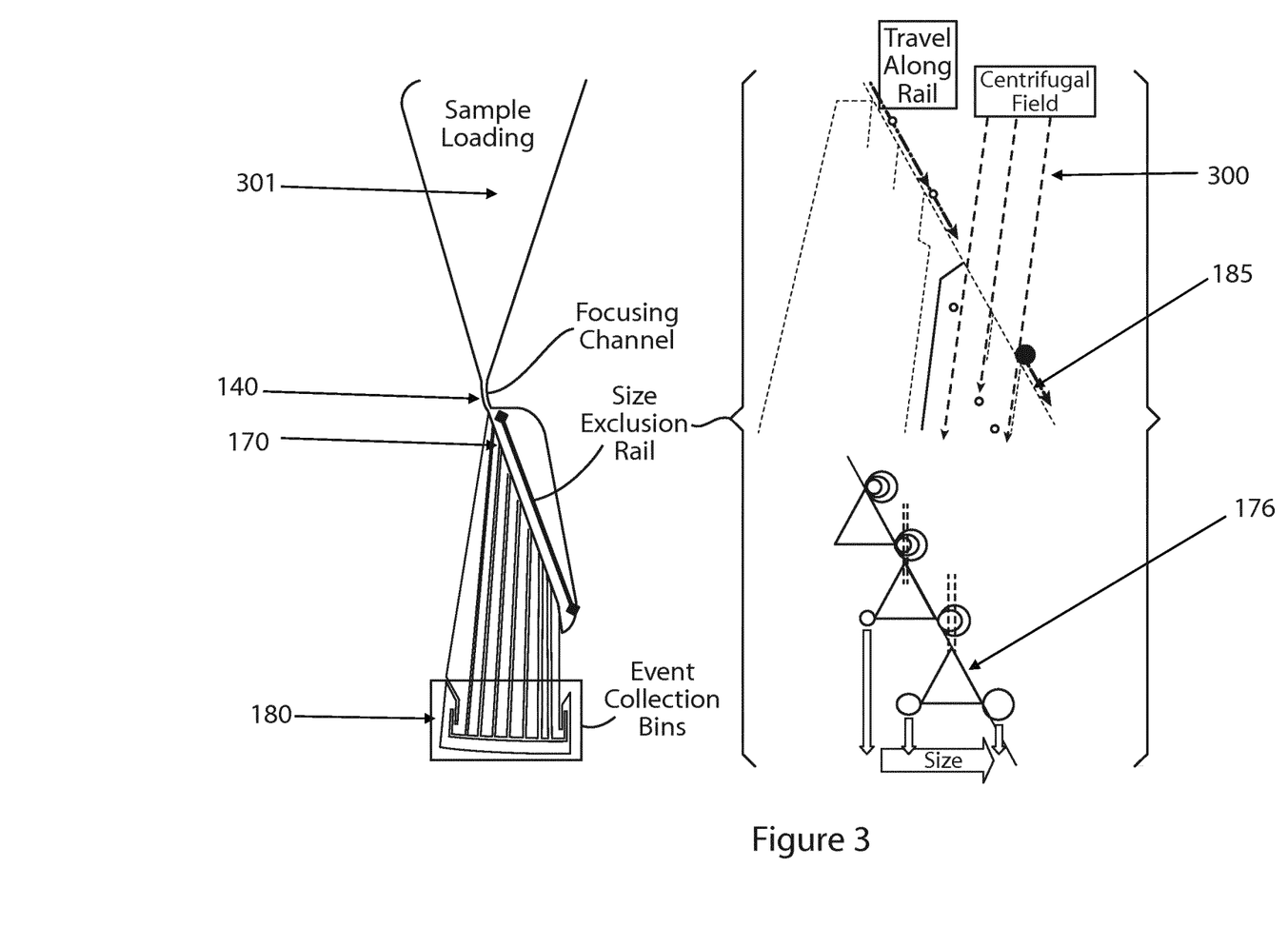
FIG. 3 is a schematic of one of the exemplary 8 chambers that were detailed in FIG. 1(*iii*) showing a sample loading area, a focusing channel, a bias rail and 8 individual collection bins.

Upon exiting the Sample Loading area through the Focusing Channel, centrifugal forces direct candidate events along the Size Exclusion Rail 170 which is inclined out of the direction of the centrifugal field; thus encouraging events to move along the rail while simultaneously experiencing a radial force 300 that pushes the event outward against the rail surface (FIG. 3). In FIG. 3 the upper section of the Size Exclusion Rail is shown zoomed to demonstrate the effect of inclining the vector of the rail (arrows indicated with numeral 185) out of the direction of the centrifugal field (arrows indicated with numeral 300), but maintaining the Event Collection Bins in the preferred embodiment essentially in alignment with the centrifugal field. Isolated events are represented by red circles. Although the rail is inclined from the centrifugal field, the angle is sufficiently shallow that events will run along the rail without being pinned to the point of immobilisation. Ideally, this angle is sufficient to ensure a balance between cell radial migration with immobilisation caused by pressing the cells against the rail by virtue of the radial centrifugal field.

As described above, the rail 170 is a segmented rail comprising a set of apertures 175 that are defined by the spacing between a series of posts 176, with the distance between the posts increasing in size along the length of the entire rail. The posts can adopt any geometrical form although in certain configuration a flat-edged triangular geometry may be preferred. Advantageously this shape corrects the aspect ratio of the pillar, thus easing the manufacturing of the cartridge using soft lithography but other shapes may be considered advantageous for different reasons.

The plurality of collection bins 180 are positioned radially outward from the Size Exclusion Rail 170, and the distance between the rail posts 176 capping each bin 180 define the apertures 175 that are selected to allow only cellular events below a critical size (and deformability) to penetrate the rail. The distance between posts increases for each bin, so as an event travels along the rail, the point at which it penetrates through to an underlying bin is indicative of the size (and deformability) of that event. The further along the event this occurs, the larger (and-or less deformable) the event is (FIGS. 1iii and 3).

It will be appreciated that in applications that have a low numbers of cells per cluster (e.g. doublets), and/or clusters (or even cell types) that significantly deviate from a circular shape (e.g. chains), the shape of the cluster has an impact on the capacity of the target particles to penetrate through the apertures.

It will be appreciated that the number of actual apertures that may be provided as a gating arrangement to a specific bin may vary and for example in FIG. 1 there are up to 3 apertures capping a single bin. Although the sizes of the apertures increase as the bin number increases, the apertures gating a single bin are the same size. As the Size Exclusion Rail is inclined from the centrifugal field, but the Event Collection Bins are aligned with the field, events will rapidly penetrate through to the Event Collection Bins when a sufficiently sized gate is encountered. This minimises the possibility of clogging.

The fluidic priming of the chambers ensures the test operates in a "stopped flow" mode. Here, the fluid in the chamber is stagnant so that no fluidic flow lines are evident (after the initial filling process completed). This is important as it thus allows the events that are below the critical width of an encountered gate in the rail to sediment into the appropriate collection bin. It will be appreciated that a size sorting mechanism in accordance with the present teaching may also work at moderate flow rates of the suspending medium. This may be particularly useful if cells get stuck on their motion along the rail. Such a "sticking" could be monitored during the sorting process and provided as a feedback to a drive controller for the rotational substrate to effect a modification of the speed of rotation.

The sizes of the gates can be adjusted according to the medically relevant range of interest to the test. However, the gates restricting entry to bin number 1 will generally be set such that only cellular debris will occupy the first bin 180A.

Data Analysis

When the spin cycle is complete, the occupancy of the Event Collection Bins 180 can be measured by microscopy (brightfield or fluorescence) to determine the extent (amount of clustering) and range (distribution of cluster sizes) present in the original sample. As cell clusters are not expected in healthy blood, it may not be necessary to additionally label the cells to identify specific medically relevant antigens when using this strategy. The detection of multi-cellular clusters at all can indicate pathologies that are of interest to medics.

Analysis Method

It will be appreciated that any one of a number of different analysis techniques may be employed. For example, the base of all collection bins can be examined microscopically and based on this analysis the bins are simply scored as either "occupied" or "non-occupied". In this way an occupied bin is given a score of 1, a non-occupied bin is given a score of 0. When these measurements are made for all chambers on the substrate, data can be condensed to a single readout using Equation 1:

$$\text{Cluster Score} = \frac{\sum (\text{Occupancy Scores per bin})}{n} \quad [\text{Equation 1}]$$

Where n=number of chambers 120 observed on the chip 110 and the sum extends over all occupied bins.

Figure 4:
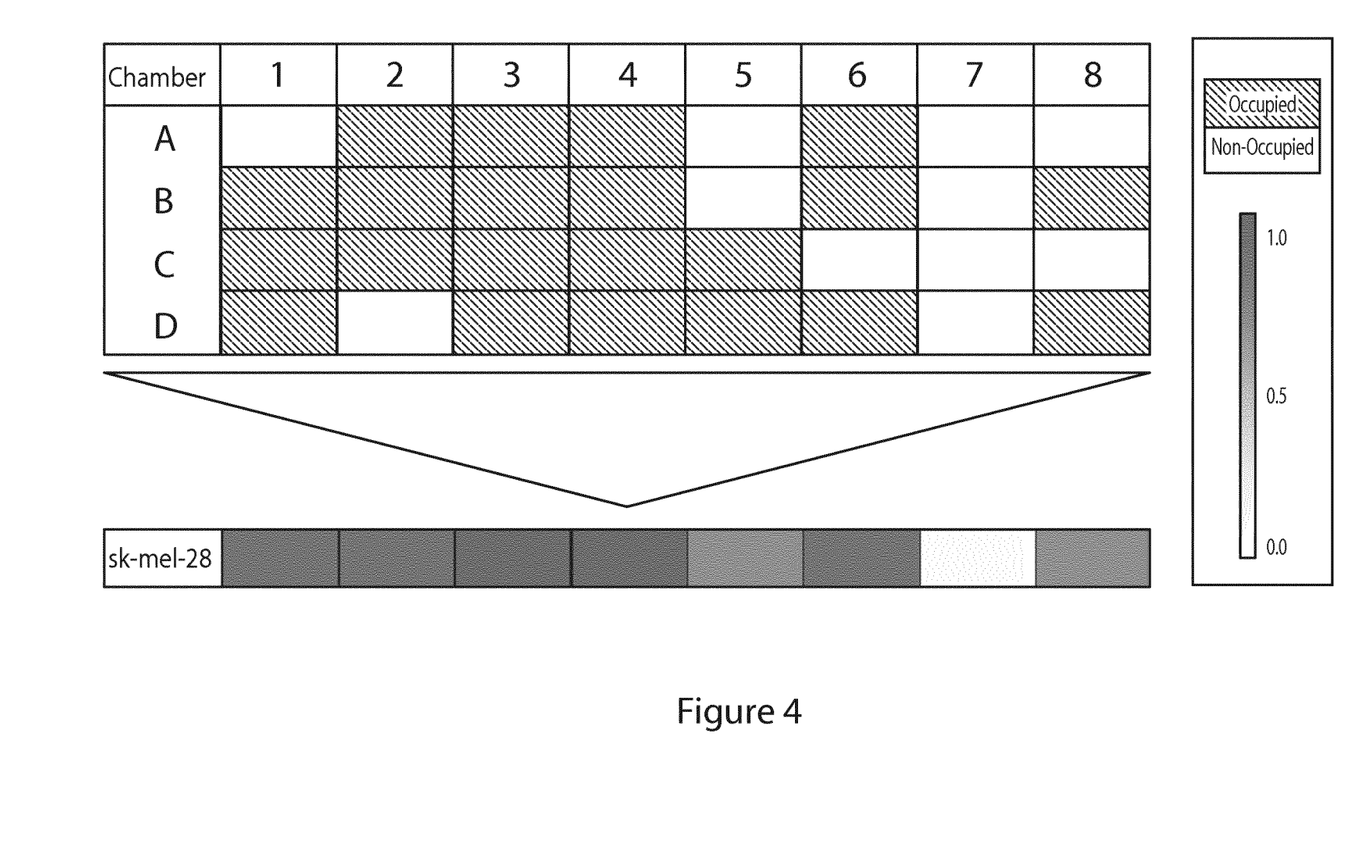
FIG. 4 is an example of a set of data that may be obtained using a device in accordance with the present teaching to determine cluster load in a sample.

An example of such analysis is shown graphically in FIG. 4 where, following completion of the spin cycle, the bins of experimental chambers were observed and scored as "occupied" (hatched) or "non-occupied" (blank). These data were summed up using Equation 1 to generate a heat-map showing the extent and range of clustering present. In this example, n=4 chambers were counted.

It will be appreciated that the above describes exemplary arrangements of a microfluidic device that have been described with reference to provision of a centrifugally driven sedimentation of particles in a fashion whereby a particle interacts with a segmented biasing rail that is inclined or angularly offset with regard to the radial direction of an induced centrifugal force. The biasing rail is segmented to include a plurality of apertures that are spaced along the rail from an axis of rotation proximal position to an axis of rotation distal position. It will be appreciated therefore that in the context of the present teaching that a segmented bias rail defines an extended element that comprises a set of apertures that are defined by the spacing between a series of posts and against which particles of interest are operably biased through a radially induced centrifugal force.

Each aperture in the rail has a radial offset to a preceding aperture and by providing apertures whose spacings vary dependent on their location on the rail it is possible to discriminately target particles of specific dimensions as they are biased toward and along the rail. It will be appreciated that the capacity of a particular target event to pass through an aperture and into the associated bin for that aperture is dependent not only on the relative sizes of the target particle and the aperture but also the capacity of the particle to deform. It will be appreciated that particles deviating from a (quasi) spherical shape, e.g. doublet- or chain-like formations, can pass through smaller gaps as long as their maximum cross section allows it that passage. In accordance with the present teaching the dimensions of the individual apertures increase along the rail such that particles of successively increasing dimensions will be allowed to pass through the rail as the particles migrate along the rail.

Each of the apertures preferably provide a collection bin for the particles that have a dimensions small enough to pass through the apertures that provide an inlet for that specific collection bin. In this way a device per the present teaching will preferentially target the smallest particles first and then target particles or clusters of particles of successively larger dimensions. The inlet for the collection bin that targets the smallest particles is in this way closest to the axis of rotation of the device and the inlet for the collection bin that targets the largest particles is furthest from the axis of rotation of the device.

Any one collection bin may have a plurality of inlets and it is desirable that the dimensions of the individual inlets of the plurality of inlets for a particular collection bin are at least similar and preferably identical. In this way particles having a dimension less than the dimensions of the inlets will pass through the inlets into that particular bin whereas particles having dimensions larger than the dimensions of individual inlets will be biased along the rail until the next set of inlets until they either pass into a collection bin whose inlet(s) are sufficiently large to allow passage of those particles or are not captured by the segmented rail arrangement.

It will be understood that individual apertures are formed by gaps between obstacles that are defined in the rail. In the same way that the rail defines a plurality of apertures it will be appreciated that the physical elements between the apertures define obstacles. The obstacles may be dimensioned to preferentially bias or direct particles towards the apertures that neighbour the rails. To achieve the increasing dimension of the apertures along the length of the rail, the absolute gap spacing to next obstacle increases in size so that constrictions are formed between the radially offset obstacles which laterally deflect larger particles while smaller particles penetrate through the gaps in the radial direction.

It will be appreciated that the shape of the exemplary obstacles shown in the Figures is a triangular shape. The present inventors have realised that this shape is particularly advantageous when the device is fabricated using lithographic techniques and that use of different fabrication techniques such as for example injection moulding, CNC etc., may result in different shaped obstacles being used.

Desirably the obstacles are configured such that they do not project out of the axis of the rail so as to obviate potential issues of sedimentation clogging due to the stopped-flow nature of the fluidics. Furthermore such projections could create a "ski-jump" effect whereby a target particle may be redirected by such a projection beyond the bin that was intended to capture that particle. However, such a projection could be used to target particular particles.

While the angles of the triangular posts illustrated are particularly acute, it will be appreciated that the edges of each of the triangular posts on the distal edge of the post (on the downstream side of the fluidic inlet) to direct any event destined to penetrate the gate slightly below the next post. This could be used to minimize some clogging that can occur when a number of events try to penetrate an aperture in a short time—they can jam between the end point of one post, and the start point of the next.

Using an arrangement per the present teaching it is possible to provide, through a series of such constrictions which are separated by gaps or apertures of increasing gap sizes, a size/deformability sorting of a population of particles. The particles that are suitably sized to pass through apertures into the inlets of specific collection bins are then collected in discrete collection bins.

It will be understood that the segmented rail is desirably offset from a radial axis so as to slope away from axis of rotation. Particles that are biased by the induced centrifugal force in a direction along a radial axis from the axis of rotation encounter the biasing rail and then are maintained proximal to that rail until such time as they either pass through an appropriate gap in the rail to a particular collection bin or travel the length of the rail and away from contact from the rail.

A device provided in accordance with the present teaching may be provided in stopped-flow mode or stagnant flow conditions whereby a fixed volume of liquid is introduced into a specific microchannel and through rotation of device, any particles within that fixed volume are separated into size-specific collection bins. The quantification of size distribution is achieved by collecting particles in an array of bins and the level of discrimination in that distribution can be determined by the number of collection bins and the dimension of the inlet(s) that form the entrance to those bins.

The particles can be beads, cells or clusters of cells.

Therefore it will be appreciated and understood that a microfluidic device per the present teaching may be used in a number of applications and it is not intended to limit the present teaching to any one set of applications or uses except as may be deemed necessary in the light of the following claims.

The words comprises/comprising when used in this specification are to specify the presence of stated features, integers, steps or components but does not preclude the presence or addition of one or more other features, integers, steps, components or groups thereof.

The invention claimed is:

1. A microfluidic device to be provided on a rotatable substrate, the substrate being rotatable about an axis of rotation so as to operably provide a centrifugal force that propels particles of interest from a location proximal an axis of rotation of the substrate towards a circumference of the substrate, the microfluidic device comprising:
   a sorting chamber, the sorting chamber comprising an inlet through which a fluid comprising particles of interest may operably be introduced, a segmented bias rail defining a plurality of apertures that determine dimensions of specific particles of interest that may pass through the segmented rail into individual ones of a plurality of collection bins positioned radially outwardly of the rail; the segmented bias rail being inclined relative to the direction of the centrifugal force; wherein access to individual ones of the plurality of collection bins is determined by dimensions of the apertures defined by the rail, each of the apertures providing an inlet for a corresponding collection bin and the dimensions of the apertures determine the size of particles of interest that may pass through a specific aperture and into a corresponding collection bin, and further wherein the dimensions of the apertures increase with increased radial distance away from the axis of rotation such that operably particles of interest of a first size will be collected in a first collection bin provided proximal to the axis of rotation and particles of interest of a second size will be collected in a second collection bin provided distal to the axis of rotation, the first size being smaller than the second size.

2. The microfluidic device of claim 1 wherein the particles of interest operably migrate along the rail in a stopped flow mode of operation.

3. The microfluidic device of claim 1 wherein the segmented rail comprises a plurality of posts, spacing between individual posts determining the dimensions of the apertures that define access to the collection bins.

4. The microfluidic device of claim 1 wherein the segmented rail defines a plurality of apertures for any one collection bin.

5. The microfluidic device of claim 1 wherein the collection bins are orientated parallel to force lines of the induced centrifugal force.

6. The microfluidic device of claim 5 wherein the segmented rail defines a plurality of apertures for any one collection bin.

7. The microfluidic device of claim 6 wherein the segmented rail comprises a plurality of posts, spacing between individual posts determining the dimensions of the apertures that define access to the collection bins.

8. The microfluidic device of claim 1 comprising a plurality of sorting chambers circumferentially arranged about an axis of rotation of the device such that operable rotation of the substrate provides the centrifugal force that will bias particles within the fluid that is introduced into the inlet of each sorting chamber along the respective bias rail.

9. The microfluidic device of claim 8 wherein the collection bins are orientated parallel to force lines of the induced centrifugal force.

10. The microfluidic device of claim 1 wherein the sorting chamber is orientated on or in the substrate such that the inlet of the sorting chamber is provided proximal to the axis of rotation of the substrate.

11. The microfluidic device of claim 10 wherein the segmented rail defines a plurality of apertures for any one collection bin.

12. The microfluidic device of claim 10 wherein the collection bins are orientated parallel to force lines of the induced centrifugal force.

13. The microfluidic device of claim 10 comprising a plurality of sorting chambers circumferentially arranged about an axis of rotation of the device such that operable rotation of the substrate provides the centrifugal force that will bias particles within the fluid that is introduced into the inlet of each sorting chamber along the respective bias rail.

14. The microfluidic device of claim 13 wherein the collection bins are orientated parallel to force lines of the induced centrifugal force.

15. The microfluidic device of claim 14 wherein the segmented rail defines a plurality of apertures for any one collection bin.

16. The microfluidic device of claim 15 wherein the segmented rail comprises a plurality of posts, spacing between individual posts determining the dimensions of the apertures that define access to the collection bins.

17. The microfluidic device of claim 16 configured such that particles of interest operably migrate along the rail in a stopped flow mode of operation.

18. A method of separating particles of interest into at least two collection bins, access to a specific collection bin being determined by size, the method comprising:

providing a rotatable substrate comprising a microfluidic device, the microfluidic device comprising: a sorting chamber, the sorting chamber comprising an inlet through which a fluid comprising particles of interest may operably be introduced, a segmented bias rail defining a plurality of apertures that determine dimensions of specific particles of interest that may pass through the segmented rail into individual ones of a plurality of collection bins positioned radially outwardly of the rail; the segmented bias rail being inclined relative to the direction of the centrifugal force produced by rotating the substrate; wherein access to individual ones of the plurality of collection bins is determined by dimensions of the apertures defined by the rail, each of the apertures providing an inlet for a corresponding collection bin and the dimensions of the apertures determine the size of particles of interest that may pass through a specific aperture and into a corresponding collection bin, the dimensions of the apertures increase with increased radial distance away from the axis of rotation such that operably particles of interest of a first size will be collected in a first collection bin provided proximal to the axis of rotation and particles of interest of a second size will be collected in a second collection bin provided distal to the axis of rotation, the first size being smaller than the second size;

introducing a fluid comprising particles of interest into the inlet of the sorting chamber;

rotating the substrate to provide a centrifugal force that propels the particles of interest from a location proximal an axis of rotation of the substrate towards a circumference of the substrate;

allowing individual groups of particles of interest to migrate through the segmented rail into specific ones of the plurality of collection bins, wherein each of the apertures provide an inlet for a corresponding collection bin and the dimensions of the apertures determine the size of particles of interest that may pass through a specific aperture and into the collection bin, wherein the dimensions of the apertures increase with increased radial distance away from the axis of rotation, the method further comprising:

collecting particles of interest of a first size in a first collection bin provided proximal to the axis of rotation and particles of interest of a second size in a second collection bin provided distal to the axis of rotation, the first size being smaller than the second size.

19. The method of claim 18 further comprising, prior to the introduction of the fluid containing particles of interest into the microfluidic device, generating the fluid containing the particles of interest from another fluid that contains the particles of interest and other particles.

20. The method of claim 19 wherein generating the fluid containing the particles of interest from another fluid that contains the particles of interest and other particles comprises generating the fluid containing the particles of interest via an induced magnetic field, and the particles of interest comprise circulating tumor cells.

\* \* \* \* \*